United States Patent [19]
Bonfils et al.

[11] Patent Number: 6,083,928
[45] Date of Patent: *Jul. 4, 2000

[54] SKIN HEALING METHOD

[75] Inventors: Armelle Bonfils, Conflans Sainte Honorine; Pierre Smets, Villennes sur Seine; René Zalisz, Menucourt, all of France

[73] Assignee: The Boots Company PLC, Nottingham, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/041,842

[22] Filed: Apr. 2, 1993

Related U.S. Application Data

[63] Continuation of application No. 07/540,492, Jun. 19, 1990, abandoned.

[51] Int. Cl.[7] ............................ A61K 47/36; A61K 39/02
[52] U.S. Cl. ...................... 514/54; 424/236.1; 424/241.1; 424/257.1; 424/259.1; 424/260.1; 514/887
[58] Field of Search .................... 514/54, 887; 435/101; 424/236.1, 241.1, 257.1, 259.1, 260.1

[56] References Cited

U.S. PATENT DOCUMENTS

| | | | |
|---|---|---|---|
| 4,833,131 | 5/1989 | Williams et al. | 514/54 |
| 4,870,010 | 9/1989 | Hayes | 424/114 |
| 4,929,604 | 5/1990 | Munford et al. | 514/53 |
| 5,145,676 | 9/1992 | Fahey et al. | 514/2 |

FOREIGN PATENT DOCUMENTS

PCT/SE87/00502 of 0000 Sweden.

OTHER PUBLICATIONS

Copy of European Search Report (2 pages).
Copy of Gynecology & Obstertrics Article.
Copy of Derwent (C) WPIL Article (1 page).
Copy of Bacterial Products Article (1985) pp. 119–127.
Copy of Hafnia Alvei Lipopolysaccharides Article 1988.
Copy of Studies on Inflammation Article (7 pages).
Grassi et al. Int. Archs. Allergy. appl. Immunol. 76, p. 119 (1985.

*Primary Examiner*—Gollamudi S. Kishore
*Attorney, Agent, or Firm*—Arent Fox Kintner Plotkin & Kahn, PLLC

[57] ABSTRACT

A method for facilitating the healing of skin comprising applying topically to skin a composition containing an amount of a lipopolysaccharide extracted from gram negative bacteria effective to facilitate skin healing.

4 Claims, No Drawings

SKIN HEALING METHOD

PRIOR APPLICATION

This application is a continuation of U.S. patent application Ser. No. 540,492 filed Jun. 19, 1990, now abandoned.

STATE OF THE ART

The lipopolysaccharides extracted from gram negative bacteria have been described in the literature as having immunomodulatory properties; in particular they present non-specific stimulating properties for the body's defences (1985, Int. Archs Allergy Appl. Immun. 76 Suppl. 1,119–127 and Journal of Immunopharmacology 3(2), 119–132 (1981). Other pertinant prior art includes U.S. Pat. No. 4,454,119, British patent No. 856,413, Current Microbiology, Vol. 14 (1987), page 251 to 253 and FEMS Microbiology Immunology, Vol. 47, No. 3 (1988), p. 151 to 156.

OBJECTS OF THE INVENTION

It is an object of the invention to provide a novel method of healing skin.

This and other objects and advantage of the invention will become obvious from the following detailed description.

The Invention

The novel method of the invention for facilitating the healing of skin comprises topically applying to skin a composition containing an amount of a lipopolysaccharide extracted from gram negative bacteria effective to facilitate skin healing. It was unexpected that the lipopolysaccharides would have remarkable properties for cutaneous healing.

Preferably, the gram negative bacteria to be extracted are selected from the group consisting of *Klebsiella pneumoniae*, Hafnia, *Enterobacter cloacae*, *Escherichia coli*, *Klebsiella ozoenae* and *Pseudomonas aeruginosa*. Examples of specific gram negative bacteria to be extracted are *Klebsiella pneumoniae* strain No. I-163, Hafnia strain No. I-868, *Enterobacter cloacae* strain No. I-869, *Escherichia coli* strain No. I-870, type 4 encapsulated *Klebsiella ozoenae* strain No. I-871 and *Pseudomonas aeruginosa* strain No. I-872, I-873 and I-874, all available from the Pasteur Institute (Paris) and *Pseudomonas aeruginosa* strain No. 21630 from the ATCC.

The lipopolysaccharides possess remarkable healing properties in the treatment of burns of any origin, in plastic surgery, in alopecia, in the treatment of skin ulcers and in surgery.

The lipopolysaccharides show a remarkable inductive activity like the EGF (Epidermal Growth Factor) factor of epidermal growth without showing the toxicity of the latter. From this fact, the lipopolysaccharides can be used to facilitate the healing of the skin and the epidermis. Due to their remarkable healing properties, the lipopolysaccharides of the invention are useful in the treatment of burns of any origin, in the treatment of third degree burns, sunburn, superficial wounds, chapping, cracking of the skin, chilbains, insect bites, in surgery or plastic surgery to facilitate healing, in the ageing of skin, and finally in alopecia. The usual dose, variable according to the product used, the patient treated and the affection concerned, can be 50 µg to 5 mg per day by local application for a man.

The compositions may be solids or liquids and can be presented in the pharmaceutical forms currently used in human medicine such as creams, gels, ointments, lotions, milks or oils for the skin, drops, collyria, aerosols, shampoos or in the form of liposomes prepared according to standard methods. The active ingredient or ingredients can be incorporated with the excipients usually used in these pharmaceutical compositions such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

Numerous processes for the preparation of lipopolysaccharides have been described in the literature. Particularly, the article by O. Westphal and K. Jann, in Methods in Carbohydrate Chemistry (Whistler Ed., Vol. 5, p. 83, Academic Press, New York, 1965) can be referred to. The processes described most often use an extraction with a phenol/water mixture of the centrifugation deposit from the microbe culture, followed by dialysis. Examples of such preparations appear in the experimental part.

In the following examples there are described several preferred embodiments to illustrate the invention. However, it is to be understood that the invention is not intended to be limited to the specific embodiments.

EXAMPLE 1

Hafnia Lipopolysaccharides

After centrifugation of the Enterobacter hafnia culture strain deposited at the Pasteur Institute in Paris under the No. I-868, the deposit was washed twice with a solution of sodium chloride at 9% and twice with acetone. After centrifuging, the deposit was dried at 40° C. under vacuum and dissolved in distilled water at 65° C. and extracted with an equal volume of a phenol/water (90/10) mixture at 65° C. After cooling in an ice bath and centrifuging at 10,000 r/min for 30 minutes at 10° C., the aqueous phase was recovered and dialyzed under continuous flux with de-ionized water for 2 days, then lypohilized to obtain 2.32 g of Hafnia lipopolysaccharides per liter of fermentor.

EXAMPLE 2

*Klebsiella pneumoniae* Lipopolysaccharides

Using the procedure of Example 1, the non-encapsulated *Klebsiella pneumoniae* strain deposited at the Pasteur Institute in Paris under the number I-163 was treated to obtain 1.33 g of *Klebsiella pneumoniae* lipopolysaccharides per liter of fermentor.

EXAMPLE 3

*Klebsiella ozoenae* Lipopolysaccharides

Using the procedure of Example 1, the encapsulated *Klebsiella ozoenae* strain type 4 deposited at the Pasteur Institute in Paris under the number I-871 was treated to obtain 1.42 g of *Klebsiella ozoenae* lipopolysaccharides per liter of fermentor.

EXAMPLE 4

*Pseudomonae aeruginosa* Lipopolysaccharides

Using the procedure of Example 1, the *Pseudomonas aeruginosa* strain deposited at the ATCC under the number 21630 was treated to obtain 0.6 g of *Pseudomonas aeruginosa* lipopolysaccharides per liter of fermentor.

Using the procedure of Example 1, the *Pseudomonas aeruginosa* strains deposited at the Pasteur Institute under the numbers I-872, I-873, I-874, 0.8 g, 0.67 g and 0.47 g, respectively, of *Pseudomonas aeruginosa* polysaccharides per liter of fermentors were obtained.

EXAMPLE 5

A healing ointment was prepared containing 1 g of the lipopolysaccharides extracted from *Klebsiella pneumoniae* of Example 1 and sufficient excipient for a final weight of 100 g.

EXAMPLE 6

A healing ointment was prepared containing 1 g of the lipopolysaccharides extracted from Hatnia of Example 2 and sufficient excipient for a final weight of 100 g.

Study of the Healing Activity

Culture

Fibroblasts of human derma were multiplied in a monolayer culture in Eagle Medium with Earle salts (EMEM, Boeringher Laboratories) containing 10% of fetal calf serum (Flow Laboratories) and the experiments were carried out with cultures varying from 7 to 10 passages. 30 ml three-dimensional gels were created by mixing 13.8 ml of EMEM (concentrated 1.76 times), 2.7 ml of fetal calf serum or of EMEM (according to the experiments), 9 ml of acid-soluble collagen extracted from the tendons of rats' tails (3 mg/ml in acetic acid 1/1000), 1.5 ml of 0.1N NaOH and 3 ml of a suspension of fibroblasts in EMEM ($4 \times 10^5$ cells/ml). This mixture was placed at 37° C. in 100 mm diameter bacteriology Petri dishes to allow polymerization of the collagen and formation of a gel in which the fibroblasts were distributed in three dimensions.

1 mm diameter circular biopsies were taken from healthy skin fragments resulting from remedial surgery (mammaplasty performed on 20 to 45 year old women). According to the experiments, these biopsies were implanted in the middle of the artificial derma once the gel had formed, or stuck with a drop of collagen to the derma, the contraction of which had stabilized on the 5th day. In the latter case, the implant was stuck either on living derma or on derma whose fibroblasts had been killed by osmotic shock before epidermization.

Treatment with Lipopolysaccharides

The lipopolysaccharide studied was dissolved at the moment of treatment in fetal calf serum, so that it had a final concentration in the culture of 0.0005%, 0.005%, , 0.05%, 0.5%, and 5%. The lipopolysaccharide was added on the 5th day, once the fibroblasts had modified the collagen matrix, and therefore the treatment with the lipopolysaccharide had no further effect on this function. The total duration of the treatment was 13 days and the medium was renewed, with or without lipopolysaccharides, twice a week, taking care that the cultures were always immersed. In all the experiments, there were 3 examples of the different samples.

Quantiative Evaluation of the Epidermization

At the end of each experiment, the artificial skins were transferred into 60 mm diameter Petri dishes, incubated for one hour at 37° C. in 3 ml of culture medium containing 1 μCi/ml of tritiated thymidine ($6^{-3}$H Thymidine, 25 Ci/mM CEA). The specimens were incubated for 30 minutes at 37° C. in Nile blue sulfate (Sigma) at a final concentration of 1/10000, and rinsed for 15 minutes at the temperature of the laboratory in NaCl 9%, which allowed the epidermis which had developed on the surface of the artificial derma starting from the initial implant to be seen. The epidermized surface was then measured by planimetry using a scanner (Nachet NS 1000).

The study was carried out comparatively with cultures in the absence of and in the presence of EGF (20 mg/ml). The results which appear in Table I are the average of 3 determinations and show that the lipopolysaccharides of the invention are powerful growth factors, often more effective than EGF in the stimulation of epidermal growth.

TABLE I

| | | | Surface in $mm^2$ | | |
| Product studied | Control without EGF | EGF Control 20 mg/ml | Lipopolysaccharides | | |
| --- | --- | --- | --- | --- | --- |
| | | | 0.5 μg/ml | 5 μg/ml | 50 μg/ml |
| — | 16.36 | 109.16 | | | |
| Ex. 2 | | | 59.30 | 89.05 | 135.11 |
| Ex. 1 | | | 50.07 | 88.27 | 176.19 |
| — | 24.51 | 111.44 | | | |
| Ex. 2 | | | | 73.07 | |
| Ex. 1 | | | — | 167.00 | |
| — | 13.72 | 118.81 | | | |
| Ex. 2 | | | | | 101.21 |
| Ex. 1 | | | | | 100.95 |

Various modifications of the method of the invention may be made without departing from the spirit or scope thereof and it is to be understood that the invention is intended to be limited only as defined in the appended claims.

What is claimed is:

1. A method for increasing epidermal proliferation of skin suffering from burns, skin ulcers and surgical wounds needing increased epidermal proliferation comprising applying topically to the skin of a patient in need of increased epidermal proliferation a composition containing an amount of a liposaccharide extracted from *Klebsiella pneumoniae* strain No. I-163 of the Pasteur Institute effective to increase epidermal proliferation.

2. The method of claim 1, wherein the amount of liposaccharide applied topically to the skin is 50 μg to 5 mg per day.

3. A method for increasing epidermal proliferation of skin suffering from burns, skin ulcers and surgical wounds needing increased epidermal proliferation comprising applying topically to the skin of a patient in need of increased epidermal proliferation a composition containing an amount of a liposaccharide extracted from Hafnia strain No. I-868 of the Pasteur Institute effective to increase epidermal proliferation.

4. The method of claim 3, wherein the amount of liposaccharide applied topically to the skin is 50 μg to 5 mg per day.

* * * * *